United States Patent
Cao et al.

(10) Patent No.: US 9,814,734 B2
(45) Date of Patent: Nov. 14, 2017

(54) BUFALIN LIPOSOME, PREPARATION METHOD THEREFOR AND APPLICATION THEREOF

(71) Applicant: THE FOURTH MILITARY MEDICAL UNIVERSITY, Xi'an (CN)

(72) Inventors: Wei Cao, Xi'an (CN); Siwang Wang, Xi'an (CN); Ying Li, Xi'an (CN); Yanhua Xie, Xi'an (CN); Qian Yang, Xi'an (CN)

(73) Assignee: The Fourth Military Medical University, Shaanxi (CN)

( * ) Notice: Subject to any disclaimer, the term of this patent is extended or adjusted under 35 U.S.C. 154(b) by 137 days.

(21) Appl. No.: 14/653,234

(22) PCT Filed: Mar. 29, 2013

(86) PCT No.: PCT/CN2013/073466
§ 371 (c)(1),
(2) Date: Jun. 17, 2015

(87) PCT Pub. No.: WO2014/101356
PCT Pub. Date: Jul. 3, 2014

(65) Prior Publication Data
US 2015/0328234 A1    Nov. 19, 2015

(30) Foreign Application Priority Data

Dec. 26, 2012 (CN) .......................... 2012 1 0570744

(51) Int. Cl.
| | | |
|---|---|---|
| *A61K 9/127* | (2006.01) | |
| *A61K 31/585* | (2006.01) | |
| *A61K 31/58* | (2006.01) | |
| *A61K 9/00* | (2006.01) | |
| *A61K 9/20* | (2006.01) | |

(52) U.S. Cl.
CPC .......... *A61K 31/585* (2013.01); *A61K 9/0019* (2013.01); *A61K 9/1271* (2013.01); *A61K 9/1272* (2013.01); *A61K 9/1277* (2013.01); *A61K 31/58* (2013.01); *A61K 9/2013* (2013.01); *A61K 9/2018* (2013.01); *A61K 9/2059* (2013.01)

(58) Field of Classification Search
CPC .................................................... A61K 9/127
See application file for complete search history.

(56) References Cited

U.S. PATENT DOCUMENTS

| | | | |
|---|---|---|---|
| 3,134,772 A | 5/1964 | Kondo et al. | |
| 3,687,944 A | 8/1972 | Pettit et al. | |
| 5,605,703 A | 2/1997 | Lambiez et al. | |
| 6,472,507 B1* | 10/2002 | Fischer ............ | A61K 47/48238 530/326 |
| 7,744,920 B2* | 6/2010 | Barenholz ............ | A61K 9/1271 424/450 |

FOREIGN PATENT DOCUMENTS

| | | |
|---|---|---|
| CN | 101732349 A | 6/2010 |
| CN | 102038690 A | 5/2011 |
| CN | 102302475 A | 1/2012 |
| CN | 102600180 A | 7/2012 |
| EP | 1325739 B1 | 3/2006 |

OTHER PUBLICATIONS

Dai et al (Antitumor effect of Venenum Bufonis liposome injection, Journal of Shenyang Pharmaceutical University, Sep. 2007, English Abstract).*
Tse-Chao et al (Freeze-drying pharameuctical and Food Products, 2010, p. 211).*
Amano et al., "Increased nuclear expression and transactivation of vitamin D receptor by the cardiotonic steroid bufalin in human myeloid leukemia cells", Journal of Steroid Biochemistry & Molecular Biology, 114, (2009) 144-151.
Bick et al., "Effects of Chan Su, a traditional Chinese medicine, on the calcium transients of isolated cardiomyocytes: Cardiotoxicity due to more than Na, K-ATPase blocking", Life Sciences, 72, (2002) 699-709.
Dasgupta et al., "Neutralization of Cardiac Toxins Oleandrin, Oleandrigenin, and Cinobufatalin by Digibind: Monitoring the Effect by Measuring Free Digitoxin Concentrations", Life Sciences, vol. 63, No. 9, 781-788, 1988.
Gong et al., "Progress on Pharmacological Action and Preparation of Venenum Bufonis" Food and Drug, 2007, 51-53.
Han et al., "Anti-tumor activities and apoptosis-regulated mechanisms of bufalin on the orthotopic transplantation tumor model of human hepatocellular carcinoma in nude mice", World J Gastroenterol Jun. 28, 2007; 13(24): 3374-3379.
Kostakis et al., "Sudden death associated with intravenous injection of toad extract", Forensic Science International, 188, (2009) e1-e5.
Li et al., "PI3K/Akt is involved in bufalin-induced apoptosis in gastric cancer cells", Anti-Cancer Drugs 2009, vol. 20 No. 1, 59-64.
Meng et al., "Pilot Study of Huachansu in Patients with Hepatocellular Carcinoma, Non-Small Cell Lung Cancer, or Pancreatic Cancer", Cancer. Nov. 15, 2009; 115(22): 5309-5318.
Numanzawa et al., "Involvement of Na+, K+-ATPase Inhibition in K562 Cell Differentiation Induced by Bufalin", Journal of Cellular Physiology, 160: 113-120, 1994.

(Continued)

*Primary Examiner* — Benjamin Packard
(74) *Attorney, Agent, or Firm* — Dorsey & Whitney LLP

(57) ABSTRACT

The present invention provides a bufalin liposome comprising a liposome bilayer and bufalin. The liposome bilayer comprises phospholipid, sterol and polyethylene glycol (PEG)-derived compound. The liposome of the present invention can be used to treat cancer, especially a cancer chosen from liver cancer, lung cancer, ovarian cancer, prostate cancer, colon cancer, pancreas cancer, gastric cancer, and leukemia. The preparation method of the present invention is simple, and the bufalin liposome can increase an effect of antitumor, reduce a toxicity compared with bufalin monomer, and has wide applications.

21 Claims, No Drawings

(56) References Cited

OTHER PUBLICATIONS

Pan et al., "In Vivo Antitumor Activity of Folate Receptor-targeted Liposomal Daunorubicin in a Murine Leukemia Model", Anticancer Research 25: 343-346 (2005).

Qin et al., "Efficacy and safety of gemcitabine-oxaliplatin combined with huachansu in patients with advanced gallbladder carcinoma", World J Gastroenterol Sep. 7, 2008; 14(33): 5210-5216.

Safra, "Cardiac Safety of Lipsomal Anthracyclines", The Oncologist, 2003, 8 (suppl 2) 17-24.

Shmeeda et al., "Intracellular uptake and intracavitary targeting of folateconjugated liposomes in a mouse lymphoma model with up-regulated folate receptors", Mol Cancer Ther, 2006; 5(4). Apr. 2006.

Sun et al., "Bufalin Induces Reactive Oxygen Species Dependent Bax Translocation and Apoptosis in ASTC-a-1 Cells", Hindawi Publishing Corporation Evidence-Based Complementary and Alternative Medicine Volume, 2011, Article ID 249090, 1-12.

Takai et al., "Bufalin induces growth inhibition, cell cycle arrest and apoptosis in human endometrial and ovarian cancer cells", International Journal of Molecular Medicine, 21: 637-643, 2008.

Vingerhoeds et al., "Immunoliposome-mediated targeting of doxorubicin to human ovarian carcinoma in vitro and in vivo", British Journal of Cancer (1996) 74, 1023-1029.

Xie et al., "Bufalin induces autophagy-mediated cell death in human colon cancer cells through reactive oxygen species generation and JNK activation", Free Radical Biology & Medicine, 51 (2011) 1365-1375.

Yang et al., "Bufalin enhances the anti-proliferative effect of sorafenib on human hepatocellular carcinoma cells through downregulation of ERK", Mol Biol Rep (2012) 39:1683-1689.

Yeh et al., "Effects of Bufalin andCinobufagin onthe Proliferation of Androgen Dependent and Independent Prostate Cancer Cells", TheProstate 54:112-124 (2003).

Yin et al., "Bufalin induces apoptosis in human osteosarcoma U-2OS and U-2OS methotrexate300-resistant cell lines", Acta Pharmacol Sin May 2007; 28 (5): 712-720.

Yu et al., "Apoptotic signaling in bufalin- and cinobufagin-treated androgen-dependent and -independent human prostate cancer cells", Cancer Sci, Dec. 2008, vol. 99, No. 12, 2467-2476.

Zalipsky et al., Peptide Attachment to Extremities of Liposomal Surface Grafted PEG Chains: Preparation of the Long-Circulating Form of Laminin Pentapeptide, YIGSR, Bioconjugate Chem. 1995, 6, 705-708.

Zhu et al., "Bufalin Induces Lung Cancer Cell Apoptosis via the Inhibition of Pl3K/Akt Pathway", Int. J. Mol. Sci. 2012, 13, 2025-2035.

International Search Report from International Application No. PCT/CN2013/073466 dated Oct. 3, 2013.

\* cited by examiner

BUFALIN LIPOSOME, PREPARATION METHOD THEREFOR AND APPLICATION THEREOF

TECHNICAL FIELD

The invention belongs to the technical field of medicine, and relates to a bufalin liposome, the preparation method and the application thereof.

BACKGROUND ART

Cancer is one of the diseases with highest incidence in the world. WHO data shows that just in 2008, the number of people who died of cancer reaches up to 760 million, in which 60% come from low-income or middle-income countries and the number will increasingly grow in future. Among more than 200 kinds of cancers, patients with breast cancer, lung cancer, intestinal cancer and pancreas cancer account for 54% of all newly increased cases. At present, the methods for the treatment of cancers mainly comprise surgery, radiotherapy, chemotherapy and the combination thereof according to the types and stages of cancers. There are a number of chemotherapeutic drugs used today. The most common chemotherapy agents act by killing fast-dividing cells, one of the main properties of most cancer cells. Therefore, such drugs can also kill other normal rapidly-dividing cells, such as cells in bone marrow, digestive tract and hair follicles while killing rapidly-dividing cancer cells, and thus generate serious side effect and damage normal tissues. Hence there is a need to develop a new therapeutic drug with small toxic and side effect and hight antitumor efficacy. The dominant strategy for the development of new antitumor drugs is to improve the tumor selectivity of a drug to tumor and to reduce the distribution thereof in normal tissues.

Bufalin (3β,14-dihydroxy-5β, 20(22)-bufadienolide, 5β,20(22)-bufadienolide-3β,14-diol), a main antitumor ingredient in *Venenum Bufonis* that is a kind of traditional Chinese medicine, is white serous fluid secreted from the parotid gland of *Bufo bufo gargarizans* or *Bufo melanostictus*, and can be extracted from *Venenum Bufonis*. Also, it can be artificially synthesized according to U.S. Pat. Nos. 3,134,772 and 3,687,944. Bufalin is digoxin-like immunoreactive ingredient, and shows various bioactivities such as heart strengthening, anesthetization and vascular stimulation. Since the discovery of the antitumor effect of bufalin in 1994 (Numazawa S, et al. J Cell Physiol, 1994, 160(1): 113-20), a large number of studies have been made, which have found that it has broad-spectrum antitumor effect. Additionally, bufalin exhibits chemosensitization effect on tumor cells in combination with other chemotherapeutic drugs such as Sorafenib and the like (Gao Y, et al. Mol Biol Rep. 2012, 39(2):1683-9). In recent years, there have been more researches that have found bufalin can induce cell apoptosis so as to inhibit the proliferation of various cancer cells such as cells of liver cancer, bone tumor, colon cancer, lung cancer, pancreas cancer, ovarian cancer, gastric cancer, prostate cancer and leukemia (Han K Q, et al. World J Gastroenterol. 2007, 13(24):3374-9; Amano Y, et al. J Steroid Biochem Mol Biol. 2009, 114(3-5):144-51; Li D, et al. Anticancer Drugs. 2009, 20(1):59-64; Yu C H, et al. Cancer Sci. 2008, 99(12):2467-76; Takai N, et al. Int J Mol Med. 2008, 21(5):637-43; Yeh J Y, et al. Prostate. 2003, 54(2):112-24; Yin J Q, et al. Acta Pharmacol Sin. 2007, 28(5):712-20; Zhu Z et al. Int. J. Mol. Sci. Int J Mol Sci. 2012, 13(2):2025-35; Xie C M, et al. Free Radic Biol Med. 2011, 51(7):1365-75). Bufalin can trigger cancer cell apoptosis by activating cell death receptor and mitochondrion pathway (Sun L, et al. Evid Based Complement Alternat Med. Epub 2011 Jun. 18). These studies hint that bufalin can be used as a chemotherapeutic drug for the treatment of cancers. However, due to high toxicity, poor water solubility, short half-life, narrow therapeutic window and the toxic dosage and therapeutic dose being close, the clinical application of bufalin is severely restricted (Gong L L et al. Food and Drug. 2007, 9(10):51-3). Moreover, since it is widely distributed in vivo, other clinical side effects, such as vascular stimulation, anaphylactic shock, hyperpyrexia, sinus bradycardia, etc., are further induced (Dasgupta A, et al. Life Sci. 1998, 63(9):781-8; Bick R J, et al. Life Sci. 2002, 72(6):699-709; Kostakis C, Byard R W. Forensic Sci Int. 2009, 188:e1-e5).

At present, a Huachasu injection, prepared by dissolving *Venenum Bufonis* in normal saline, has been used for the clinical treatment of cancer in China. It has been reported that the combination of gemcitabine-oxaliplatin with Huachasu can enhance the chemotherapeutic effect in the treatment of patients with advanced gallbladder cancer (Qin T J, et al. World J Gastroenterol. 2008, 14(33):5210-6). Other studies show that the Huachasu injection did not produced obvious toxicity when administered to a patient with liver cancer or pancreas cancer in 8-fold standard dose (20 ml/m²/day or 20-25 ml/person/day, containing 14.3±0.03 ng/ml of bufalin) (Meng Z. et al. Cancer, 2009, 115(22):5309-18), which means that the effective therapeutic amount of bufalin tolerated by an adult patient every day can reach up to 2.3 μg. However, the Huachasu injection is a mixture solution of alkaloids in *Venenum Bufonis*, and the content of bufalin contained therein is very low due to the poor water solubility of bufalin.

Therefore, it is very necessary to develop a new dosage form which can prolong the duration of bufalin in tumor focus, improve tumor targeting and reduce toxic and side effect.

Liposome has a closed phospholipid dilayer structure with internal water phase. We adopt liposome as the drug carrier of bufalin to solve the problem of poor water solubility thereof by loading bufalin with phospholipid membrane. Additionally, the PEG-modified liposome can allow bufalin to passively target to tumor site so as to reduce the toxic and side effects thereof.

In the last 20 years, liposome was widely used for encapsulating antitumor agents. There have been various antitumor liposome drugs used or to be used clinically, such as doxorubicin liposome (Doxil/Caelyx is sold by Alza/Johnson and Johnson in America or by Schering-Plough in other countries respectively), daunorubicin liposome (DaunoXome, Gilead), cytarabine liposome (DepoCyte, produced by Skye Pharma/Enzon/Mundipharma) and cisplatinum liposome (Lipoplatin, produced by Regulon), wherein the cytarabine liposome can be used for the treatment of meningeal lymphoma. The liposome can improve the solubility of an anti-cancer drug with poor water solubility through phospholipid membrane structure, and realize the passive tumor targeting by PEG modification and the active tumor targeting by conjugating with a carrier.

Conventional liposome is formed by dispersing phospholipid in water phase, thus amphipathic and lipid-soluble agents can be inserted into the phospholipid membrane structure of liposome, whereas hydrophilic agents are directly encapsulated into the internal water phase of liposome. The liposome carrier has a great influence on the pharmacokinetics, distribution in tissue, and toxic and side effect of the encapsulated agent. For example, clinical tests prove that the toxic effect of doxorubicin liposome is significantly reduced as compared with that of doxorubicin monomer while maintaining antitumor activity (Safra T. Oncologist. 2003, 8 Suppl 2:17-24).

However, since the liposome can be rapidly captured by macrophage, its retention time in vivo after administration is only several hours. In order to improve the circulating half-life of liposome in vivo, glycolipids or hydrophilic polymers such as PEG can be applied to liposome. PEG, a biocompatible polymer, is conjugated onto the liposome to enable it to have a protective hydrophilic surface, and the liposome thus obtained is known as "second-generation liposome" or "stealth liposome". PEG results in steric hindance effect on the surface of liposome so as to hinder the adsorption of opsonins and plasma proteins and reduce the binding of macrophage receptors to phosphate groups on the phospholipid membrane, and thereby prolongs the retention time thereof in blood circulation.

Furthermore, the pharmacokinetic property of liposome can be changed by chemically modifying the surface of liposome with phospholipid groups or binding proteins, polypeptides or other macromolecules. PEG liposomes with conjugated carriers such as micromolecules, peptides or monoclonal antibodies have been widely used in the tumor treatment, e.g. folic acid-conjugated daunorubicin and doxorubicin liposomes (Pan X Q, Lee R J. Anticancer Res. 2005, 25(1A):343-6; Shmeeda H, et al. Mol Cancer Ther. 2006, 5(4):818-24), laminin liposome (Zalipsky S, et al. Bioconjug Chem. 1995, 6(6):705-8) or OV-TL3 monoclonal antibody-conjugated liposome (Vingerhoeds M H, et al. Br J Cancer. 1996, 74(7):1023-9).

So far, there hasn't been any report about bufalin liposome. For this purpose, the present invention is provided.

SUMMARY OF THE INVENTION

The first object of the present invention is to provide bufalin liposome, so as to further improve the therapeutic effect of bufalin formulation and generalize the application of bufalin in the prevention and treatment of tumor.

For achieving the first object, the present invention adopts following technical solutions:

A bufalin liposome consists of a liposome bilayer and bufalin, the liposome bilayer comprising a phospholipid, sterol and polyethyleneglycol (PEG)-derived compound.

The bufalin liposome bilayer of the present invention preferably comprises a phospholipid, sterol and PEG-derived compound simultaneously, wherein the content of phospholipid accounts for 20-80%, preferably 40-60% of the total weight of liposome bilayer. The phospholipid is selected from lecithin, phosphatidylcholine (PC), phosphatidylethanolamine (PE), phosphatidyl glycerol (PG), phosphatidylinositol, phosphatidylserine, sphingomyelin (SM), dipalmitoyl phosphatidyl choline (DPPC), dipalmitoyl phosphatidyl ethanolamine (DPPE), distearoyl phosphatidylcholine (DSPC) or any mixture of the above.

In the present invention, the content of the sterol accounts for 10-30%, preferably 15-20% of the total weight of liposome bilayer. The selectable sterol is cholesterol, epicholesterol, ergosterol or stigmasterol. Preferably, the sterol used is cholesterol.

In the present invention, the content of the PEG-derived compound accounts for 2-50%, preferably 20-40% of the total weight of liposome bilayer. The selectable PEG-derived compound is PEG-PE, methoxy polyethylene glycol (mPEG)-PE, cholesterol PEG modifier or distearoyl phosphatidyl ethanolamine (DSPE)-PEG or any mixture of the above.

In the bufalin liposome of the present invention, the weight ratio of the liposome bilayer to bufalin is (5-20):1, preferably (8-12):1.

The second object of the present invention is to provide a preparation method of the above bufalin liposome.

The bufalin liposome of the present invention can be prepared via conventional methods, but considering the effects of preparation method on the formulation itself, the present invention preferably adopts any one of thin-film method, injection method, thin-film method combined with freeze-thaw method and injection method combined with freeze-thaw method.

The thin-film method of the present invention comprises following steps: dissolving bufalin and liposome bilayer materials (i.e. phospholipid, sterol and PEG-derived compound) in non-polar or weak-polar solvent separately or simultaneously, and homogeneously mixing, removing organic solvent under reduced pressure by a rotary evaporator to form uniform thin film on the wall of a flask, followed by adding distilled water or buffer solution to hydrate the thin film, and then subjecting to homogenization, stirring, vortexing and/or ultrasonic treatment to obtain the bufalin liposome.

Among these steps, the homogenization, stirring, vortexing and ultrasonic treatment can be performed either simultaneously or partially. In the above operations, the rotary evaporation temperature is 20-60° C., the hydrating duration is 15-240 min and the hydration temperature is 20-65° C., and the ultrasonic duration is 5-60 min; and preferably, the rotary evaporation temperature is 30-40° C., the hydrating duration is 60-90 min and the hydration temperature is 35-50° C., and the ultrasonic duration is 20-40 min.

The mass-to-volume ratio of bufalin to the organic solvent in the present invention is 0.1-1 mg/ml. The non-polar or weak-polar solvent is selected from methanol, ethanol, chloroform, ethyl acetate, n-hexane, acetonitrile or any mixture of the above solution, preferably chloroform and/or methanol. The pH value of the buffer solution is 6.4-7.4.

The injection method of the present invention comprises following steps: dissolving liposome bilayer materials (phospholipid, sterol and PEG-derived compound) and bufalin in an organic solvent, injecting the solution into distilled water or a buffer solution with an injector after complete dissolution, and stirring at 20-60° C. for 0.5-4 h to completely remove the organic solvent so as to obtain the bufalin liposome.

Among these steps, after completely removing the organic solvent, homogenization, stirring, vortexing and/or ultrasonic treatment can also be further performed to improve the encapsulation efficiency.

Specifically, the injection method also mainly comprises ethanol injection method and diethyl ether injection method according to the types of solvents.

The ethanol injection method comprises following steps: dissolving liposome bilayer materials (phospholipid, sterol and PEG-derived compound) and bufalin in ethanol, injecting the solution into distilled water or a buffer solution with an injector after complete dissolution, stirring to completely remove the ethanol, and optionally performing further homogenization, stirring, vortexing and/or ultrasonic treatment to obtain the bufalin liposome.

The diethyl ether injection method comprises following steps: dissolving liposome bilayer materials (phospholipid, sterol and PEG-derived compound) and bufalin in diethyl ether or a mixture of diethyl ether and methanol, injecting the solution into distilled water or a buffer solution with an injector after complete dissolution, stirring to completely remove diethyl ether, and optionally performing further homogenization, stirring, vortexing or ultrasonic treatment to obtain the bufalin liposome.

The buffer solution is normal saline, phosphate buffer solution (PBS), tris(hydroxymethyl)aminomethane hydrochloride (Tris-HCl) solution, 4-hydroxyethylpiperazine ethanesulfonic acid (HEPES) solution or mannitol solution.

For further improving the encapsulation efficiency, the present invention also can prepare the bufalin liposome by adopting thin-film method combined with freeze-thaw method and injection method combined with freeze-thaw method.

The thin-film method combined with freeze-thaw method and the injection method combined with freeze-thaw method of the present invention comprise following steps: freezing the bufalin liposome obtained by the thin-film method or the injection method in a 0-(−80)° C. refrigerator or liquid nitrogen for 2-24 h, thawing at room temperature, re-freezing in the 0-(−80)° C. refrigerator or liquid nitrogen, thawing at room temperature, repeating the freeze-thawing for 2-8 times to obtain the bufalin liposome after freeze-thawing. Preferably, the methods comprise freezing the bufalin liposome obtained by the thin-film method or the injection method in a (−20)-(−40)° C. refrigerator or liquid nitrogen for 5-10 h, thawing at room temperature, re-freezing in the (−20)-(−40)° C. refrigerator or liquid nitrogen, thawing at room temperature and repeating the freeze-thawing for 4-6 times.

In the above methods, the water phase can be distilled water or a buffer solution, such as normal saline, PBS, Tris-HCl solution, HEPES solution or mannitol solution. The pH of the buffer solution is 5.0-9.5.

After the liposome of the present invention is prepared, the particle size distribution thereof can be controlled by filtering through suitable filters. By passing through a film with pore diameter of 5 μm, 1 μm, 100 nm, 200 nm or other desired pore diameters, the liposome with corresponding particle size can be obtained. The specific operation is mastered by a skilled person in the art.

The third object of the present invention is to provide a pharmaceutical composition comprising the above bufalin liposome.

The bufalin liposome of the present invention can be used for preparing drugs for the treatment of cancers. For example, it can be prepared into tablet, capsule, granule, pill, syrup, water aqua or suspension for oral administration.

The tablet of the present invention is composed of bufalin liposome, a diluting agent, an adhesive and a lubricant. The adhesive is selected from one or more of dextrin, PVP adhesive slurry and gelatin slurry. The diluting agent is selected from one or more of microcrystalline cellulose, starch and lactose. The lubricant is selected from one of talcum powder and magnesium stearate.

In the above tablet, the weight ratio of raw materials preferably is: bufalin liposome:starch:lactose:dextrin:magnesium stearate of (0.1-10):(0.5-50):(0.4-40):(0.1-20):(0.1-2), wherein the weight of the bufalin liposome is counted as that of bufalin raw material.

The tablet of the present invention can be obtained by using the preparation method in the prior art, but more ideally, prepared by using following method: dissolving the bufalin liposome in an appropriate amount of water, freeze-drying, then adding starch and lactose, mixing well, adding the aqueous solution of dextrin to prepare soft material, sieving and granulating, drying at 50° C., molding, adding magnesium stearate, mixing well and tabletting. The "appropriate amount" herein can be understood by the skilled person in the art, and counted as g/ml in the present invention; preferably, the volume of water used is 2-10 fold weight of the bufalin. For example, if 5 g of bufalin is used as raw material to prepare the bufalin liposome, it will be dissolved in 50 ml of water during the preparation method. In addition, specific freeze-drying, tabletting, etc. are mastered by the skilled person in the art, so the present invention does not specifically give definitions.

In another embodiment of the present invention, the composition can also be freeze-dried powder injection, which consists of the bufalin liposome, a dispersing agent and a freeze-drying adjuvant. The dispersing agent is selected from one of poloxamer, Tween-80 and Span-65, preferably poloxamer. The freeze-drying adjuvant is selected from one or more of mannitol, injectable lactose, injectable glucose, dextranum and saccharose, preferably saccharose.

In the freeze-dried powder injection of the present invention, the weight ratio of raw materials preferably is: bufalin liposome:poloxamer:saccharose of (0.1-20):(0.4-40):(0.1-40), wherein the weight of bufalin liposome is counted as that of bufalin raw material.

The above freeze-dried powder injection can be prepared by adopting preferably, but not limited to, following method: dissolving the bufalin liposome in an appropriate amount of water, adding the dispersing agent and freeze-drying adjuvant, filtering with a microporous filter film after complete dissolution, subpackaging, charging nitrogen, and encapsulating. The dispersing agent and the freeze-dried adjuvant preferably are poloxamer and saccharose.

For parenteral administration or intravenous, intraperitoneal, intramuscular or subcutaneous administration, the normal saline can be used as pharmaceutically acceptable solvent. Other solvents include distilled water, buffer solution and 0.3% glycine solution. The formulation can be sterilized via conventional methods such as ultraviolet radiation or passing through a film, and then freeze-dried for storage. For achieving physiological environment requirement, a pharmaceutically acceptable pH regulator and pressure regulator, such as sodium chloride, sodium acetate or potassium salts, etc are required to be added.

In order to improve the stability of liposome, phospholipid oxidation inhibitor, including vitamins or derivatives thereof, butylated hydroxytoluene (BHT), chroman, ferrioxamine or any mixture of the above, can also be added with reference to U.S. Pat. No. 5,605,703 and EP1325739.

In order to improve oral bioavailability, polysaccharide polymers, including chitosan, starch, dextran, pullulan, pectin or any mixture of the above, can also be added.

Moreover, the present invention further seeks protection of use of the said bufalin liposome in the preparation of a drug for the treatment of cancers.

The bufalin is a kind of effective anti-cancer drug, however, the use thereof is restricted due to high toxicity thereof. The inventors firstly found that the bufalin liposome could reduce the toxicity while enhancing anti-cancer effect. By acting on mammals via intravenous injection, intraperitoneal injection, intramuscular injection, subcutaneous injection or oral administration, the bufalin liposome has enhanced anti-cancer effect and reduced toxic and side effect compared to bufalin monomer.

The bufalin liposome of the present invention can be used for the treatment of cancers, such as liver cancer, lung cancer, ovarian cancer, prostate cancer, colon cancer, pancreas cancer, gastric cancer or leukemia.

The dosage of drug needs to be administered according to the diagnosis of diseases and the judgment of clinician, generally 0.01-50 mg/kg, and preferably 0.1-5 mg/kg.

By adopting the above technical solutions, the present invention obtains a bufalin liposome, and the preparation method, composition and application thereof. The bufalin liposome has good stability, and can significantly improve the therapeutic effect thereof in preventing and treating cancers compared to bufalin monomer or other formulations. Furthermore, the preparation method of the present invention is simple and has low production cost, which facilitate generalization and application.

DETAILED EMBODIMENTS

The following examples are intended to illustrate the present invention, but not to limit the scope of the present invention.

EXAMPLE 1

Thin-Film Method 5 mg of bufalin is dissolved in 5 ml of ethanol, and 40 mg of phospholipid, 15 mg of cholesterol and 5 mg of DSPE-PEG are dissolved in chloroform, followed by mixing the organic solution in a round-bottom flask, rotary-evaporating at 30° C. under reduced pressure to remove residual organic solvent so as to form a uniform thin film on the wall of the flask. Adding 5 ml PBS (5 mM, pH 6.4-7.4) onto the uniform thin film, hydrating at 50° C. for 1 h, and performing ultrasonic treatment for 0.5 h, the liposome is prepared.

The prepared liposome is dialyzed in 1 L of water for 24 h, followed by collecting small amount of liposome, demulsifying by adding methanol, and measuring the encapsulation efficiency via HPLC. The encapsulation efficiency of the obtained bufalin liposome is 58.7% (the encapsulation efficiency is the proportion of encapsulated drug amount in phospholipid based on the total amount of drug added).

EXAMPLE 2

Thin-Film Method

Compared to Example 1, the difference only lies in that in this Example, normal saline is used instead of PBS. The encapsulation efficiency of the obtained bufalin liposome is 57.3%.

EXAMPLE 3

Thin-Film Method

Compared to Example 1, the difference only lies in that in this Example, 6% mannitol water solution is used instead of PBS. The encapsulation efficiency of the obtained bufalin liposome is 38.4%.

EXAMPLE 4

Thin-Film Method

Compared to Example 1, the difference only lies in that in this Example, the volume of PBS (5 mM, pH 6.4-7.4) added is 40 ml and the hydration is conducted at 60° C. for 3 h. The encapsulation efficiency of the obtained bufalin liposome is 49.3%.

EXAMPLE 5

Thin-Film Method 4 mg of bufalin, 5 mg of cholesterol, 40 mg of granulesten and 5 mg of mPEG-PE are dissolved in 10 ml of chloroform:methanol (2:1), followed by rotary-evaporating the solution under reduced pressure to remove the residual organic solvent, adding 1 ml PBS (5 mM, pH 6.4-7.4), violently whirling, and performing ultrasonic treatment in ice bath for 20 min. The encapsulation efficiency of the obtained bufalin liposome is 52.5%.

EXAMPLE 6

Thin-Film Method

Compared to Example 5, the difference only lies in that in this Example, the dosage of granulesten is 10 mg. The encapsulation efficiency of the obtained bufalin liposome is 38.64%.

EXAMPLE 7

Thin-Film Method

Compared to Example 5, the difference only lies in that in this Example, the phospholipid is egg yolk lecithin. The encapsulation efficiency of the obtained bufalin liposome is 51.45%.

EXAMPLE 8

Thin-Film Method

Compared to Example 5, the difference only lies in that in this Example, the PEG-derived compound of cholesteryl hemisuccinate (CHEMS-PEG) is used instead of mPEG-PE. The encapsulation efficiency of the obtained bufalin liposome is 54.08%.

EXAMPLE 9

Thin-Film Method

Compared to Example 5, the difference only lies in that in this Example, the weight ratio of liposome bilayer to bufalin is 8:1. Specifically, bufalin is 6.25 mg, cholesterol is 5 mg, granulesten is 40 mg and mPEG-PE is 5 mg. The encapsulation efficiency of the obtained bufalin liposome is 65.47%.

EXAMPLE 10

Thin-Film Method

Compared to Example 5, the difference only lies in that in this Example, the weight ratio of liposome bilayer to bufalin is 12:1. Specifically, bufalin is 4.17 mg, cholesterol is 5 mg, granulesten is 40 mg and mPEG-PE is 5 mg. The encapsulation efficiency of the obtained bufalin liposome is 53.86%.

EXAMPLE 11

Thin-Film Method

Compared to Example 5, the difference only lies in that in this Example, the weight ratio of liposome bilayer to bufalin is 5:1. Specifically, bufalin is 10 mg, cholesterol is 5 mg, soyabean lecithin is 40 mg and mPEG-PE is 5 mg. The encapsulation efficiency of the obtained bufalin liposome is 34.39%.

EXAMPLE 12

Thin-Film Method

Compared to Example 5, the difference only lies in that in this Example, the weight ratio of liposome bilayer to bufalin is 20:1. Specifically, bufalin is 2.5 mg, cholesterol is 5 mg, soyabean lecithin is 40 mg and mPEG-PE is 5 mg. The encapsulation efficiency of the obtained bufalin liposome is 30.54%.

EXAMPLE 13

Injection Method 4 mg of bufalin, 6 mg of cholesterol, 30 mg of phospholipid and 4 mg of mPEG-PE are dissolved in 10 ml of ethanol, and the solution is subjected to ultrasonic treatment for 20 min until completely dissolved. The solution is injected by an injector into 20 ml PBS (5 mM, pH 6.4-7.4), followed by stirring at 50° C. for 3 h to remove ethanol. The encapsulation efficiency of the obtained bufalin liposome is 83.3%.

EXAMPLE 14

Injection Method 4 mg of Bufalin, 15 mg of cholesterol, 40 mg of phospholipid and 5 mg of mPEG-PE are dissolved in 10 ml of diethyl ether, and the solution is subjected to ultrasonic treatment for 20 min until completely dissolved. The solution is injected by an injector into 20 ml of 6% mannitol solution, followed by stirring at 50° C. for 3 h to remove diethyl ether. The encapsulation efficiency of the obtained bufalin liposome is 56.8%.

EXAMPLE 15

Thin-Film Method Combined with Freeze-Thaw Method 4 mg of bufalin, 6 mg of cholesterol, 30 mg of phospholipid and 4 mg of mPEG-PE are dissolved in 10 ml of chloroform: methanol (2:1), followed by rotary-evaporating the solution under reduced pressure to remove the residual organic solvent, adding 1 ml PBS (5 mM, pH 6.4-7.4), violently vortexing, performing ultrasonic treatment in ice bath for 20 min, freezing for 5 h in a −20° C. refrigerator, placing at room temperature for thawing, re-freezing in the refrigerator, and repeating the freeze-thawing for 4 times. The encapsulation efficiency of the obtained bufalin liposome is 61.8%.

EXAMPLE 16

Injection Method Combined with Freeze-Thaw Method 4 mg of bufalin, 15 mg of cholesterol, 40 mg of phospholipid and 5 mg of mPEG-PE are dissolved in 10 ml of diethyl ether, and the solution is subjected to ultrasonic treatment for 20 min until completely dissolved. The solution is injected by an injector into 20 ml of 6% mannitol solution, followed by stirring at 50° C. for 3 h to remove diethyl ether, freezing for 4 h in a −80° C. refrigerator, placing at room temperature for thawing, re-freezing in the refrigerator, and repeating the freeze-thawing for 2 times. The encapsulation efficiency of the obtained bufalin liposome is 56.8%.

EXAMPLE 17

Compared to Example 16, the difference only lies in that in this Example, the formulation of liposome includes: 4 mg of bufalin, 6 mg of stigmasterol, 30 mg of lecithin and 5 mg of mPEG-PE. The encapsulation efficiency of the obtained bufalin liposome is 45.2%.

EXAMPLE 18

Powder Injection 5 g of bufalin is taken, followed by preparing liposome according to the method of Example 1, diluting with water to constant volume of 1,000 ml, adding 20 g of poloxamer and 100 g of saccharose, filtering with a 0.22 µm milliporous filter film after complete dissolution, subpackaging into 500 bottles (each of 2 ml), freeze-drying, charging nitrogen, and encapsulating.

EXAMPLE 19

Compared to Example 18, the difference only lies in that in this Example, the dosages of raw materials are: bufalin liposome:poloxamer:saccharose of 1:4:50.

EXAMPLE 20

Compared to Example 18, the difference only lies in that in this Example, the dosages of raw materials are: bufalin liposome:poloxamer:saccharose of 2:4:4.

EXAMPLE 21

Compared to Example 18, the difference only lies in that in this Example, the dosages of raw materials are: bufalin liposome:Span-65:mannitol of 1:2:40.

EXAMPLE 22

Compared to Example 18, the difference only lies in that in this Example, the dosages of raw materials are: bufalin liposome:Tween-80:mannitol of 2:3:4.

EXAMPLE 23

Injection 5 g of bufalin is taken, followed by preparing liposome according to the method of Example 1, diluting with normal saline to constant volume of 10,000 ml, filtering with a 0.22 μm milliporous filter film, subpackaging into 100 bottles (each of 100 ml), charging nitrogen, and encapsulating.

EXAMPLE 24

Granule 5 g of Bufalin is taken, followed by preparing liposome according to the method of Example 1, diluting with water to constant volume of 50 ml, freeze-drying, adding 50 g of starch and 35 g of sugar powder, mixing well, then adding well-mixed ethanol, dextrin and water (40:2:60) (containing 5 g of dextrin) for adhesion to prepare soft material, sieving with a 16 mesh sieve, drying at 50° C., molding, and subpackaging into 100 bags.

EXAMPLE 25

Tablet 5 g of bufalin is taken, followed by preparing liposome according to the method of Example 1, diluting with water to constant volume of 50 ml, freeze-drying, adding 40 g of starch and 10 g of lactose, mixing well, then adding the aqueous solution of 2% dextrin (total 150 ml) to prepare soft material, sieving with a 20 mesh sieve to granulate, drying at 50° C., molding with the 20 mesh sieve, adding magnesium 0.2 g of magnesium stearate, mixing well, and tabletting into 100 tablets.

EXAMPLE 26

Compared to Example 25, the difference only lies in that in this example, the formulation includes: bufalin liposome: starch: lactose:dextrin:magnesium stearate of 0.5:20:0.4:6:2.

EXAMPLE 27

Compared to Example 25, the difference only lies in that in this example, the formulation includes: bufalin liposome: starch:lactose:dextrin:magnesium stearate of 10:50:40:20:2.

EXAMPLE 28

Compared to Example 25, the difference only lies in that in this example, the formulation includes: bufalin liposome: starch:lactose:dextrin:magnesium stearate of 5:12:20:10:1.

EXAMPLE 29

Compared to Example 25, the difference only lies in that in this example, the formulation includes: bufalin liposome: starch:lactose:gelatin slurry:magnesium stearate of 5:30:10: 10:0.5.

EXAMPLE 30

Compared to Example 25, the difference only lies in that in this example, the formulation includes: bufalin liposome: starch:microcrystalline cellulose:PVP adhesive slurry:talcum powder of 5:33:5:6:1.5.

The stability of the liposome of the present invention and the therapeutic effect thereof on cancer are further illustrated by following test examples.

TEST EXAMPLE 1

Stability Test of Bufalin Liposome

The bufalin liposomes prepared in Example 1 are placed under conditions of 4° C. and 37° C., and after different durations, the various indexes are determined. The variation of each index is given in Table 1. As seen from the results, the bufalin liposome has good stability after placed both at 4° C. and 37° C. for 24 h respectively; and after storage under relative humidity of 75% at 37° C. for 3 months, both of the particle size and surface potential have no obvious variation, the encapsulation efficiency is slightly reduced, and the overall stability is good.

TABLE 1

| Temperature | | Duration | | | | |
| --- | --- | --- | --- | --- | --- | --- |
| | | 1 h | 2 h | 4 h | 8 h | 24 h |
| 4° C. | Particle size (nm) | 187 ± 10 | 180 ± 7.2 | 185 ± 11 | 197 ± 4.7 | 188 ± 10 |
| | Potential (mV) | −14.4 ± 3.3 | −13.3 ± 1.3 | −13.7 ± 1.8 | −13.3 ± 1.8 | −12.9 ± 1.2 |
| 37° C. | Particle size (nm) | 183 ± 9.2 | 179 ± 12 | 189 ± 6.8 | 190 ± 5.8 | 183 ± 0.8 |
| | Potential (mV) | −15.7 ± 0.4 | −14.3 ± 0.7 | −13.2 ± 3 | −13.7 ± 1.4 | −13 ± 2.8 |

The bufalin liposome prepared in Example 1 is placed under conditions of 37° C. and relative humidity (RH) of 75%, and after different durations, the various indexes are determined. The variation of each index is given in Table 2.

TABLE 2

| Property | time (month) | | | |
| --- | --- | --- | --- | --- |
| | 0 | 1 | 2 | 3 |
| Particle size (nm) | 184 ± 7.5 | 179 ± 5.3 | 182 ± 3.7 | 180 ± 4.8 |
| Potential (mV) | −14.8 ± 3.1 | −14.3 ± 2.9 | −13.9 ± 4.1 | −14.5 ± 5.2 |
| Encapsulation efficiency | 67.3% | 64.7% | 65.2% | 61.9% |

The above stability test is repeated for other examples, and the results show that the overall stability of the bufalin liposome prepared by the present invention is good, wherein Example 1 shows an optimal effect.

TEST EXAMPLE 2

Growth Inhibition Effect of Bufalin and Bufalin Liposome on Tumor Cells

The cells of human cervical carcinoma Hela, lung cancer A549, gastric cancer SGC7901, liver cancer HepG2, myeloid leukemia HL-60 and colon cancer SW1116 are cultured in DMEM or RPMI 1640 medium (containing 10% inactived fetal bovine serum, 100 U·ml$^{-1}$ penicillin and 100 mg·l$^{-1}$ streptomycin) in a humidified 5% $CO_2$ atmosphere at 37 V. The cells in logarithmic phase are collected, inoculated into 96-well plate at a density of $3\times10^3$/well (each well of 100 μl), and cultured for 24 h under 37° C., 5% $CO_2$ and saturated humidity condition. A negative control group (culture solution) and administration groups with different concentrations are set up for the test. 1-300 nmol/l bufalin or bufalin liposome (prepared according to the method of Example 1) is added into each culture well, followed by culturing in an incubator under 37° C., 5% $CO_2$ and saturated humidity for 48 h, adding 20 μl of MTT solution (5 g/l) into each well, culturing for 4 h, and centrifuging. The supernatant was aspirated, and 150 μl dimethyl sulfoxide (DMSO) is added to each well and slightly shaking to dissolve crystal. The OD values are measured at 570 nm by an automatic microplate reader, and the cell growth inhibition rates are calculated according to following formula: cell growth inhibition rate/%=100−(OD value of administration group−OD value of blank control group)/(OD value of control group−OD value of bland control group)×100. $IC_{50}$ (drug concentration at 50% inhibition on cell proliferation) value is calculated using mathematical method. Data are expressed as $\bar{X}\pm SEM$. Statistical significance (P<0.05) for each variable is estimated by Student's t-test or ANOVA analysis.

As seen from the results of Tables 3-4, within the concentration range of 1-300 nmol/l, both of bufalin and bufalin liposome can obviously inhibit the proliferation of the six tumor cells, and such inhibition effect is concentration dependent. The difference between the $IC_{50}$ values of bufalin and bufalin liposome is not significant, indicating that the in vitro antitumor effects of bufalin and bufalin liposome are equivalent.

TABLE 3

Inhibition effect of bufalin on the proliferation of tumor cell

| Concentration (nmol/l) | Inhibition rate (%) | | | | | |
|---|---|---|---|---|---|---|
| | HeLa | A549 | SGC-7901 | HepG2 | HL60 | SW1116 |
| 0 | 0.0 ± 0.0 | 0.1 ± 0.6 | 0.4 ± 0.3 | 0.2 ± 0.7 | 0.1 ± 0.8 | 0.1 ± 0.6 |
| 1 | 3.8 ± 2.0 | 2.0 ± 0.2 | 3.1 ± 0.5 | 5.3 ± 2.2* | 1.6 ± 0.1 | 1.9 ± 0.3 |
| 3 | 9.6 ± 8.2* | 8.5 ± 1.0* | 3.9 ± 0.8* | 6.1 ± 2.3* | 4.4 ± 0.7* | 2.7 ± 0.1* |
| 10 | 33.9 ± 4.5* | 25.3 ± 3.8* | 23.7 ± 3.6* | 30.2 ± 2.9* | 33.8 ± 6.1* | 18.0 ± 3.9* |
| 30 | 56.3 ± 8.2* | 44.2 ± 7.1* | 45.9 ± 6.5* | 49.8 ± 8.3* | 52.4 ± 8.0* | 42.7 ± 6.3* |
| 100 | 90.3 ± 10.7* | 52.3 ± 8.3* | 85.6 ± 10.2* | 69.8 ± 7.5* | 88.7 ± 9.8* | 73.1 ± 8.8* |
| 300 | 95.1 ± 6.9* | 63.8 ± 7.9* | 97.9 ± 11.3* | 87.7 ± 9.6* | 98.0 ± 10.2* | 99.4 ± 11.6* |
| IC50 | 17.1 | 78.8 | 23.5 | 33.0 | 21.1 | 30.6 |

*P < 0.05, compared to 0 nmol/l group.

TABLE 4

Inhibition effect of bufalin liposome on the proliferation of tumor cell

| Concentration (nmol/l) | Inhibition rate (%) | | | | | |
|---|---|---|---|---|---|---|
| | HeLa | A549 | SGC-7901 | HepG2 | HL60 | SW1116 |
| 0 | 1.0 ± 0.3 | 0.2 ± 0.3 | 0.0 ± 0.1 | 0.3 ± 0.6 | 1.1 ± 0.5 | 0.5 ± 0.7 |
| 1 | 5.7 ± 0.9 | 3.8 ± 0.7 | 3.6 ± 0.9 | 7.2 ± 1.1* | 2.3 ± 0.1 | 2.2 ± 0.3 |
| 3 | 11.1 ± 0.2* | 6.6 ± 1.1* | 4.7 ± 0.9* | 9.9 ± 1.8* | 6.2 ± 0.8* | 12.7 ± 0.9* |
| 10 | 38.3 ± 5.1* | 29.4 ± 3.5* | 20.2 ± 2.8* | 35.8 ± 6.0* | 28.0 ± 3.7* | 20.6 ± 4.5* |
| 30 | 62.7 ± 7.3* | 41.1 ± 6.8* | 47.3 ± 5.1* | 45.6 ± 3.4* | 44.1 ± 6.7* | 46.7 ± 6.3* |
| 100 | 94.1 ± 11.5* | 55.2 ± 7.3* | 87.3 ± 9.9* | 73.3 ± 8.6* | 79.9 ± 8.2* | 81.6 ± 9.8* |
| 300 | 98.3 ± 10.1* | 67.0 ± 8.7* | 96.4 ± 12.0* | 90.5 ± 10.3* | 94.5 ± 10.5* | 99.3 ± 11.2* |
| IC50 | 14.1 | 72.2 | 24.8 | 26.5 | 27.8 | 23.0 |

*P < 0.05, compared to 0 nmol/l group.

TEST EXAMPLE 3

Evaluation of Acute Toxicities of Bufalin and Bufalin Liposome

Male Balb/c mice (20-25 g) are purchased from the Laboratory Animal Center of Fourth Military Medical University. Bufalin is dissolved with anhydrous ethanol first, and then diluted with normal saline to 0.2 mg/ml (the final concentration of ethanol is below 1%). Bufalin liposome (prepared according to the method of Example 1) is directly dissolved in normal saline to obtain 0.2 mg/ml solution. 10 animals of each group are intraperitoneally injected with bufalin or bufalin liposome at dosages of 0.5, 1, 2, 4 and 6 mg/kg respectively (the dosage is the amount of bufalin in liposome, and the actual dosage of liposome is calculated from encapsulation efficiency). The mortality of mice, the toxic effect and any adverse reactions such as diarrhea, weight loss and behavior change are observed continuously for 7 days. The half-lethal dose ($LD_{50}$) is calculated using graphical Bliss method. The results shows that the $LD_{50}$ of bufalin and bufalin liposome are 2.0 mg/kg and 4.2 mg/kg respectively; and the toxicity and the lethality rate of the bufalin liposome are lower than those of bufalin.

TEST EXAMPLE 4

Comparison of In Vivo Therapeutic Effect of Bufalin, Huachasu Injection and Bufalin Liposome on Liver Cancer Human hepatocellular carcinoma cells, HepG2, are cultured in DMEM medium supplemented with 10% FBS, 100 U/ml penicillin G, and 100 μg/ml streptomycin in a humidified 5% $CO_2$ atmosphere at 37° C. Male BALB/c nude mice (6-week-aged) are fed in pathogen-free conditions. The bufalin liposome is prepared according to the method of Example 1. Exponentially growing $HepG_2$ cells are collected, and prepared into cell suspension with PBS. 0.2 ml of the cell suspension ($2 \times 10^7$ cells) is injected subcutaneously into the right back of each mouse. When the tumor grows to 100 mm³ (about one week), the mice are randomly divided into 4 groups (8 mice for each group), and intraperitoneally injected with 0.9% normal saline (control group), bufalin or bufalin liposome at the same dosage (Example 1, 1 mg/kg, the dosage is the amount of bufalin in liposome, and the actual dosage of liposome is calculated from encapsulation efficiency) and Huachasu injection (1 ml/kg, the dosage is obtained by converting clinically commonly used dosage into mouse administration dosage) respectively every day. Starting from injection of drugs, general conditions such as feeding, activity and body mass of the mouse are observed every two days, and the maximal diameter of tumor and the minimal diameter vertical thereto are measured by a compass and a vernier caliper. The tumor volume is calculated according to the formula: $V(mm^3)=(maximal\ diameter \times minimal\ diameter^2)/2$. After 14 days, the mice are sacrificed in anesthesia with overdose of pentobarbital sodium, followed by completely stripping the tumor body and weighing, and calculating the tumor inhibition rate by: tumor inhibition rate (%)=(average tumor weight of control group-average tumor weight of administration group)/average tumor weight of control group×100. Data are expressed as $\overline{X} \pm SEM$, and statistically processed via t-test or variance analysis. P<0.05 indicates that the two groups have significant difference therebetween.

The results are shown in Table 5: prior to administration, the tumor volumes of the three groups do not have obvious difference. But at day 14, the tumors in mice of control group grow rapidly, and the average tumor volume reaches 4097.2±821.6 mm³; in contrast, the Huachasu injection, bufalin and bufalin liposome can significantly reduce the growth of tumor, and the respective tumor volumes are 3191.5±551.8, 3205.6±711.5 and 2356.1±503.3 mm³ (P<0.05). The tumor inhibition rates of the Huachasu injection, bufalin and bufalin liposome are 22.1%, 21.8% and 42.5% respectively. It can be seen that the bufalin liposome has stronger antitumor effect as compared with bufalin monomer and Huachasu injection. Additionally, by monitoring the weights of mice and observing the toxicities in lung, liver and kidney, it is shown that such dosage of bufalin liposome has no obvious toxicity.

TABLE 5

Evaluation of in vivo therapeutic effects of bufalin, Huachasu injection and bufalin liposome on HepG2 tumour bearing mice.

| Treatment time (day) | Tumor volume (mm³) | | | |
|---|---|---|---|---|
| | Bufalin | Bufalin liposome | Control group | Huachasu injection |
| 0 | 410.5 ± 75.3 | 421.2 ± 76.8 | 413.8 ± 87.2 | 405.2 ± 63.8 |
| 2 | 1055.8 ± 203.0 | 879.3 ± 168.9 | 1215.5 ± 286.7 | 989.6 ± 179.3 |
| 4 | 1621.0 ± 303.8 | 1327.9 ± 296.8* | 1870.2 ± 379.3 | 1493.2 ± 225.7 |
| 6 | 2215.9 ± 338.1* | 1576.3 ± 315.2* | 2853.5 ± 492.1 | 2026.0 ± 286.1 |
| 8 | 2115.7 ± 349.7* | 1328.6 ± 300.8* | 2966.0 ± 415.3 | 2090.8 ± 315.3 |
| 10 | 2565.4 ± 385.2* | 1807.7 ± 349.8* | 3417.1 ± 519.8 | 2397.1 ± 320.0 |
| 12 | 2691.9 ± 407.1* | 1889.5 ± 387.2* | 3402.9 ± 534.8 | 2673.8 ± 397.9 |
| 14 | 3205.6 ± 711.5* | 2356.1 ± 503.3* | 4097.2 ± 821.6 | 3191.5 ± 551.8 |

*P < 0.05, compared to control group.

TEST EXAMPLE 5

Comparison of Therapeutic Effects of Bufalin, Huachasu Injection and Bufalin Liposome on Mice Bearing L1210 Leukemia Mouse L1210 leukemia cells are subcultured intraperitoneally in ICR mouse. The bufalin liposome is prepared according to the method of Example 1. Male ICR mice (weight of 20±2 g, 5 mice in each cage) are fed in an animal room under alternative 12-hour illumination and 12-hour darkness at a constant temperature of 25° C. and allowed free access to standard laboratory diet. The mice are inoculated intraperitoneally with $1 \times 10^5$ L1210 leukemia cell suspension under sterile condition, and randomly divided into 4 groups (10 mice for each group). After 24 h, each group is intraperitoneally injected with 0.9% normal saline (control group), bufalin or bufalin liposome at the same dosage (obtained by Example 1, 1 mg/kg, the dosage is the amount of bufalin in liposome, and the actual dosage of liposome is calculated from encapsulation efficiency) and Huachasu injection (1 ml/kg, the dosage is obtained by converting clinically commonly used dosage into mouse administration dosage) respectively every day. The survival situations of mice within 35 days are observed and recorded, and the life extension rate is calculated. Life extension rate (%)=(average survival time of administration group/average survival time of control group-1)×100. Data are expressed as $\bar{X}\pm SEM$. Statistical significance (P<0.05) for each variable was estimated by Student's t-test or ANOVA analysis.

As the results seen in Table 6, the average survival time of the animals of control group is only 16.7±1.9 days. The survival times of animals of Huachasu injection, bufalin and bufalin liposome groups are obviously prolonged, respectively 40.7%, 36.5% and 58.1%; and the average survival times thereof are 23.5±3.8, 22.8±3.1 and 26.4±3.6 days respectively. The bufalin liposome has stronger life extension effect on mice bearing L1210 leukemia compared to bufalin and Huachasu injection.

TABLE 6

Effect of bufalin, Huachasu injection and bufalin liposome on the average survival time and the life extension rate of mice bearing L1210 leukemia.

| Group | Average survival time (day) | Life extension rate (%) |
| --- | --- | --- |
| Control group | 16.7 ± 1.9 | — |
| bufalin | 22.8 ± 3.1* | 36.5 |
| bufalin liposome | 26.4 ± 3.6* | 58.1 |
| Huachasu injection | 23.5 ± 3.8* | 40.7 |

*P < 0.05, compared to control group.

The same conclusions can be obtained when repeating the above tests by using the products obtained in other Examples, and thus would not described in detail herein due to space limitation.

Although the present invention has been illustrated by aforementioned general description, specific embodiments and tests in detail, it is obvious to the skilled person in the art to make some modifications or improvements on the basis of the present invention. Therefore, such modifications or improvements, which are made without departing from the spirit of the present invention, fall into the protection scope of the present invention.

INDUSTRIAL APPLICABILITY

The present invention provides a bufalin liposome consisting of a liposome bilayer and bufalin. The liposome bilayer comprises phospholipid, sterol and PEG-derived compound. The liposome of the present invention can be used to treat cancer, especially for the treatment of liver cancer, lung cancer, ovarian cancer, prostate cancer, colon cancer, pancreas cancer, gastric cancer or leukemia. The preparation method of the present invention is simple, and the bufalin liposome obtained can increase the antitumor effect and reduce the toxic and side effect compared to bufalin monomer, and has good industrial applicability.

What is claimed is:

1. A bufalin liposome, comprising:
    a liposome bilayer comprising a phospholipid, a sterol, and a PEG-derived compound; and
    bufalin, wherein a weight ratio of the liposome bilayer to the bufalin is about 12:1;
    wherein the phospholipid accounts for about 66% of the total weight of liposome bilayer, the sterol accounts for about 25% of the total weight of the liposome bilayer, and the PEG-derived compound accounts for about 8% of the total weight of the liposome bilayer.

2. The bufalin liposome according to claim 1, wherein the phospholipid is selected from the group consisting of lecithin, phosphatidylcholine, phosphatidylethanolamine, phosphatidyl glycerol, phosphatidylinositol, phosphatidylserine, sphingomyelin, dipalmitoyl phosphatidyl choline, dipalmitoyl phosphatidyl ethanolamine, distearoyl phosphatidylcholine, and any mixture thereof.

3. The bufalin liposome according to claim 2, wherein the phospholipid is selected from the group consisting of lecithin, phosphatidylcholine, and distearoyl phosphatidylcholine.

4. The bufalin liposome according to claim 1, wherein the sterol is cholesterol.

5. The bufalin liposome according to claim 1, wherein the PEG-derived compound is selected from the group consisting of PEG-phosphatidylethanolamine, mPEG-phosphatidylethanolamine, cholesterol PEG-derived compound, DSPE-PEG, and any mixture thereof.

6. A method of making a bufalin liposome including a bufalin and a liposome bilayer comprising a phospholipid, a sterol, and a PEG-derived compound, wherein the method of making the bufalin liposome is selected from at least one of: a thin-film method, an injection method, a thin-film method combined with a freeze-thaw method, or an injection method combined with a freeze-thaw method;
    wherein a weight ratio of the liposome bilayer to the bufalin is about 12:1, the phospholipid accounts for about 66% of the total weight of liposome bilayer, the sterol accounts for about 25% of the total weight of the liposome bilayer, and the PEG-derived compound accounts for about 8% of the total weight of the liposome bilayer.

7. The method according to claim 6, wherein the thin-film method comprises:
    dissolving bufalin and liposome bilayer materials in a non-polar or a weak-polar organic solvent separately or substantially simultaneously and substantially homogeneously mixing to form a mixture;
    removing organic solvent under reduced pressure by a rotary evaporator from the mixture to form a generally uniform thin film on a wall of a flask, followed by adding distilled water or buffer solution to hydrate the generally uniform thin film; and
    subjecting to homogenization, stirring, vortexing and/or ultrasonic treatment to obtain the bufalin liposome.

8. The method according to claim 7, wherein a rotary evaporation temperature of the rotary evaporator is 20-60° C.

9. The method according to claim 7, wherein the hydrating duration is 15-240 min, and the hydration temperature is 20-65° C.

10. The method according to claim 7, wherein the ultrasonic duration is 5-60 min.

11. The method according to claim 7, wherein the mass-to-volume ratio of the bufalin to the organic solvent is 0.1-1 mg/ml.

12. The method according to claim 7, wherein the non-polar or weak-polar solvent is methanol, ethanol, chloroform, ethyl acetate, n-hexane , acetonitrile, or any mixture thereof.

13. The method according to claim 7, wherein the buffer solution is normal saline, phosphate buffer solution, Tris-HCl solution, HEPES solution, or mannitol solution; and wherein the pH value of the buffer solution is 6.4-7.4.

14. The method according to claim 7, wherein the mass-to-volume ratio of the bufalin to the buffer solution is 0.1-10 mg/ml.

15. The method according to claim 6, wherein the injection method comprises:
dissolving liposome bilayer materials and bufalin in an organic solvent;
injecting the solution into distilled water or a buffer solution with an injector after complete dissolution; and
stirring at 20-60° C. for 0.5-4 h to completely remove the organic solvent to obtain the bufalin liposome.

16. The method according to claim 15, wherein the organic solvent is one or two from ethanol, diethyl ether, or methanol.

17. The method according to claim 6, wherein the thin-film method combined with freeze-thaw method and the injection method combined with freeze-thaw method comprise:
freezing the bufalin liposome obtained by the thin-film method or the injection method in a 0-(−80)° C. refrigerator or liquid nitrogen for 2-24 h;
thawing at room temperature, re-freezing in the 0-(−80)° C. refrigerator or liquid nitrogen;
thawing at room temperature;
repeating the freeze-thawing for 2-8 times to obtain the bufalin liposome after freeze-thawing.

18. A pharmaceutical composition, comprising:
a liposome bilayer comprising a phospholipid, a sterol, and a PEG-derived compound; and
bufalin, wherein a weight ratio of the liposome bilayer to the bufalin is about 12:1;
wherein the phospholipid accounts for about 66% of the total weight of liposome bilayer, the sterol accounts for about 25% of the total weight of the liposome bilayer, and the PEG-derived compound accounts for about 8% of the total weight of the liposome bilayer.

19. The pharmaceutical composition according to claim 18, wherein the pharmaceutical composition is in the form of a tablet and a weight ratio of the raw materials in the tablet is: bufalin liposome: starch: lactose: dextrin: magnesium stearate of (0.1-10):(0.5-50):(0.4-40):(0.1-20):(0.1-2), wherein the weight of the bufalin liposome is counted as that of bufalin raw material.

20. The pharmaceutical composition according to claim 18, wherein the pharmaceutical composition is in the form of a freeze-dried powder injection and a weight ratio of the raw materials in the freeze-dried powder injection is: bufalin liposome: poloxamer: saccharose of (0.1-20):(0.4-40):(0.1-40), wherein the weight of the bufalin liposome is counted as that of bufalin raw material.

21. A method of using a bufalin liposome, the method comprising:
administering a bufalin liposome to a patient for the treatment of cancer, the cancer including at least one of liver cancer, lung carcinoma, ovarian cancer, prostate cancer, colon cancer, pancreas cancer, oesophageal cancer, gastric cancer, or leukemia;
wherein the bufalin liposome includes:
a liposome bilayer having a phospholipid, a sterol, and a PEG-derived compound; and
bufalin, wherein a weight ratio of the liposome bilayer to the bufalin is about 12:1;
wherein the phospholipid accounts for about 66% of the total weight of liposome bilayer, the sterol accounts for about 25% of the total weight of the liposome bilayer, and the PEG-derived compound accounts for about 8% of the total weight of the liposome bilayer.

* * * * *